US010966872B2

(12) United States Patent
Luckemeyer et al.

(10) Patent No.: US 10,966,872 B2
(45) Date of Patent: *Apr. 6, 2021

(54) ABSORBENT DRESSING AND METHOD

(71) Applicant: KCI Licensing, Inc., San Antonio, TX (US)

(72) Inventors: James A. Luckemeyer, San Antonio, TX (US); Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 383 days.

This patent is subject to a terminal disclaimer.

(21) Appl. No.: 15/949,656

(22) Filed: Apr. 10, 2018

(65) Prior Publication Data

US 2018/0221211 A1 Aug. 9, 2018

Related U.S. Application Data

(63) Continuation of application No. 15/276,292, filed on Sep. 26, 2016, now Pat. No. 9,968,490, which is a (Continued)

(51) Int. Cl.
*A61F 13/02* (2006.01)
*A61F 13/00* (2006.01)
*A61M 1/00* (2006.01)

(52) U.S. Cl.
CPC ...... *A61F 13/00068* (2013.01); *A61F 13/022* (2013.01); *A61F 13/025* (2013.01);
(Continued)

(58) Field of Classification Search
CPC ............ A61F 13/00068; A61F 13/0216; A61F 13/022; A61F 2013/00089–00357; A61F 2013/00361–00982; A61M 1/0088
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Australian Examination Report corresponding to Application No. 2014228670, dated Sep. 28, 2017.
(Continued)

*Primary Examiner* — Susan S Su

(57) ABSTRACT

A system that may be adapted to distribute reduced pressure to a tissue site may include a dressing and a sealing member. The dressing may include a manifold layer, a storage layer, and a plurality of retainers. The manifold layer may be adapted to be positioned proximate the tissue site, and the storage layer may be positioned proximate the manifold layer. The plurality of retainers may be disposed in the storage layer. Each of the retainers may define a fluid communication channel through the storage layer. The retainers may be adapted to substantially preclude deformation of the storage layer into the fluid communication channels. The sealing member may be adapted to cover the dressing and to provide a fluid seal between the sealing member and the tissue site.

13 Claims, 9 Drawing Sheets

Related U.S. Application Data continuation of application No. 14/179,728, filed on Feb. 13, 2014, now Pat. No. 9,474,653.

(60) Provisional application No. 61/782,528, filed on Mar. 14, 2013.

(52) U.S. Cl.
CPC ....... *A61F 13/0216* (2013.01); *A61M 1/0088* (2013.01); *Y10T 29/49826* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,340,363 A | 8/1994 | Fabo |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewell |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,468,471 B2 | 12/2008 | Sigurjonsson et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2001/0043943 A1* | 11/2001 | Coffey .......... A61L 15/225 424/447 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0027414 A1* | 2/2007 | Hoffman .......... A61M 1/0088 602/2 |
| 2007/0167926 A1 | 7/2007 | Blott et al. |
| 2009/0227969 A1 | 9/2009 | Jaeb et al. |
| 2010/0049150 A1 | 2/2010 | Braga et al. |
| 2010/0106106 A1 | 4/2010 | Heaton et al. |
| 2011/0028918 A1 | 2/2011 | Hartwell |
| 2011/0054375 A1 | 3/2011 | Smola |
| 2011/0054422 A1 | 3/2011 | Locke et al. |
| 2012/0041403 A1* | 2/2012 | Bennett .......... A61F 13/00068 604/319 |
| 2012/0136326 A1 | 5/2012 | Croizat et al. |
| 2013/0172843 A1 | 7/2013 | Kurata |
| 2014/0163491 A1 | 6/2014 | Schuessler et al. |
| 2015/0080788 A1 | 3/2015 | Blott et al. |

(56) References Cited

U.S. PATENT DOCUMENTS

| | | | |
|---|---|---|---|
| 2015/0141941 | A1 | 5/2015 | Allen et al. |
| 2015/0209200 | A1 | 7/2015 | Fouillet et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2009066106 A1 | 5/2009 |
| WO | 2010033574 A1 | 3/2010 |

OTHER PUBLICATIONS

Japanese Notice of Rejection corresponding to Application No. 2016500253, dated Nov. 7, 2017.

International Search Report and Written Opinion for corresponding PCT/US2014/016310 dated Apr. 14, 2014.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson,"An Improved Technique for Skin Graft Placement Using a Suction Drain," Surgery, Gynecology, and F.E. Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and

(56) References Cited

OTHER PUBLICATIONS

Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

ABSORBENT DRESSING AND METHOD

RELATED APPLICATIONS

This application is a Continuation of U.S. patent application Ser. No. 15/276,292, filed Sep. 26, 2016, which is a Continuation of U.S. patent application Ser. No. 14/179,728, entitled "Absorbent Dressing and Method," filed Feb. 13, 2014, now U.S. Pat. No. 9,474,653, issued Oct. 25, 2016, which claims the benefit, under 35 USC § 119(e), of the filing of U.S. Provisional Patent Application Ser. No. 61/782,528, entitled "ABSORBENT DRESSING AND METHOD," filed Mar. 14, 2013. Each of the applications referenced above are incorporated herein by reference for all purposes.

FIELD

This disclosure relates generally to medical treatment systems and, more particularly, but not by way of limitation, to absorbent dressings, systems, and methods for treating a tissue site.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Common dressings, systems, and methods may be susceptible to leaks and blockage that can cause a reduction in the effectiveness of the therapy or a complete loss of therapy. Such a situation can occur, for example, if the amount of fluid in the dressing or system exceeds the fluid capacity of the dressing or system. Thus, improvements to dressings, systems, and methods that may enhance the management of fluid extracted from a tissue site for increasing the reliability and the useable life of the dressing and system are desirable.

SUMMARY

Shortcomings with certain aspects of tissue treatment dressings, systems, and methods are addressed as shown and described in a variety of illustrative, non-limiting embodiments herein.

In some illustrative embodiments, a system for treating a tissue site may include a dressing and a sealing member. The dressing may be adapted to distribute reduced pressure from a reduced-pressure source to the tissue site. The dressing may include a manifold layer, a first storage layer, a plurality of first retainers, a second storage layer, and a plurality of second retainers. The manifold layer may be adapted to be positioned proximate the tissue site. The first storage layer may be positioned proximate the manifold layer. The plurality of first retainers may be disposed in the first storage layer. Each of the first retainers may define a first fluid communication channel through the first storage layer. The first retainers may be adapted to substantially preclude deformation of the first storage layer into the first fluid communication channels. The second storage layer may be positioned in fluid communication with the first storage layer. The plurality of second retainers may be disposed in the second storage layer. Each of the second retainers may define a second fluid communication channel through the second storage layer. The second retainers may be adapted to substantially preclude deformation of the second storage layer into the second fluid communication channels, and the second fluid communication channels may be laterally offset from the first fluid communication channels. The sealing member may be adapted to cover the dressing and to provide a fluid seal between the sealing member and the tissue site.

In other illustrative embodiments, a system for treating a tissue site may include a dressing and a sealing member. The dressing may be adapted to distribute reduced pressure from a reduced-pressure source to the tissue site. The dressing may include a manifold layer, a storage layer, and a plurality of retainers. The manifold layer may be positioned proximate the tissue site for treatment. The storage layer may be positioned proximate the manifold layer. The plurality of retainers may be disposed in the storage layer. Each of the retainers may define a fluid communication channel through the storage layer. The retainers may be adapted to substantially preclude deformation of the storage layer into the fluid communication channels. The sealing member may be adapted to cover the dressing and to provide a fluid seal between the sealing member and the tissue site.

In yet other illustrative embodiments, a system for treating a tissue site may include a dressing and a sealing member. The dressing may be adapted to distribute reduced pressure from a reduced-pressure source to the tissue site. The dressing may include a manifold layer, a first storage layer, a plurality of first fluid communication channels, a first retainer, a second storage layer, a plurality of second fluid communication channels, and a second retainer. The manifold layer may be adapted to be positioned proximate the tissue site. The first storage layer may be positioned proximate the manifold layer. The plurality of first fluid communication channels may be disposed through the first storage layer. The first retainer may be disposed in each of the first fluid communication channels. The first retainers may be adapted to substantially preclude deformation of the first storage layer into the first fluid communication channels. The second storage layer may be positioned in fluid communication with the first storage layer. The plurality of second fluid communication channels may be disposed through the second storage layer. The second retainer may be disposed in each of the second fluid communication channels. The second retainers may be adapted to substantially preclude deformation of the second storage layer into the second fluid communication channels. The second fluid communication channels may be laterally offset from the first fluid communication channels. The sealing member may be adapted to cover the dressing and to provide a fluid seal between the sealing material and the tissue site.

In yet other illustrative embodiments, a system for treating a tissue site may include a dressing and a sealing member. The dressing may be adapted to distribute reduced pressure from a reduced-pressure source to the tissue site. The dressing may include a manifold layer, a storage layer, a fluid communication channel, and a retainer. The manifold layer may be adapted to be positioned proximate the tissue site. The storage layer may be positioned proximate the manifold layer. The fluid communication channel may be disposed through the storage layer. The retainer may be disposed in the fluid communication channel. The retainer may be adapted to substantially preclude deformation of the storage layer into the fluid communication channel. The sealing member may be adapted to cover the dressing and to provide a fluid seal between the sealing member and the tissue site.

In yet other illustrative embodiments, a system for treating a tissue site may include a dressing and a sealing member. The dressing may be adapted to distribute reduced pressure from a reduced-pressure source to the tissue site. The dressing may include a manifold layer, a first storage layer, and a second storage layer. The manifold layer may be adapted to be positioned proximate the tissue site for treating the tissue site. The first storage layer may be positioned proximate the manifold layer. The first storage layer may have a plurality of first apertures disposed in the first storage layer. Each of the first apertures may define a first fluid communication channel through the first storage layer. The second storage layer may be positioned in fluid communication with the first storage layer. The second storage layer may have a plurality of second apertures disposed in the second storage layer. Each of the second apertures may define a second fluid communication channel through the second storage layer. The first fluid communication channels may be positioned laterally offset from the second fluid communication channels. The sealing member may be adapted to cover the dressing and to provide a fluid seal between the sealing member and the tissue site.

In some illustrative embodiments, a method of manufacturing a dressing may include providing a manifold material, providing an absorbent material, and positioning the manifold material adjacent the absorbent material. The method may further include cutting across the manifold material and the absorbent material to form a first storage layer and a second storage layer. The first and the second storage layer may each comprise a portion of the manifold material and the absorbent material. Further, the first storage layer may be positioned in fluid communication with the second storage layer, and the portion of manifold material in the first storage layer may be positioned laterally offset from the portion of manifold material in the second storage layer.

Other aspects, features, and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings wherein.

DETAILED DESCRIPTION OF ILLUSTRATIVE EMBODIMENTS

In the following detailed description of the non-limiting, illustrative embodiments, reference is made to the accompanying drawings that form a part hereof. Other embodiments may be utilized, and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is provided without limitation and with the scope of the illustrative embodiments being defined by the appended claims.

Figure 1:
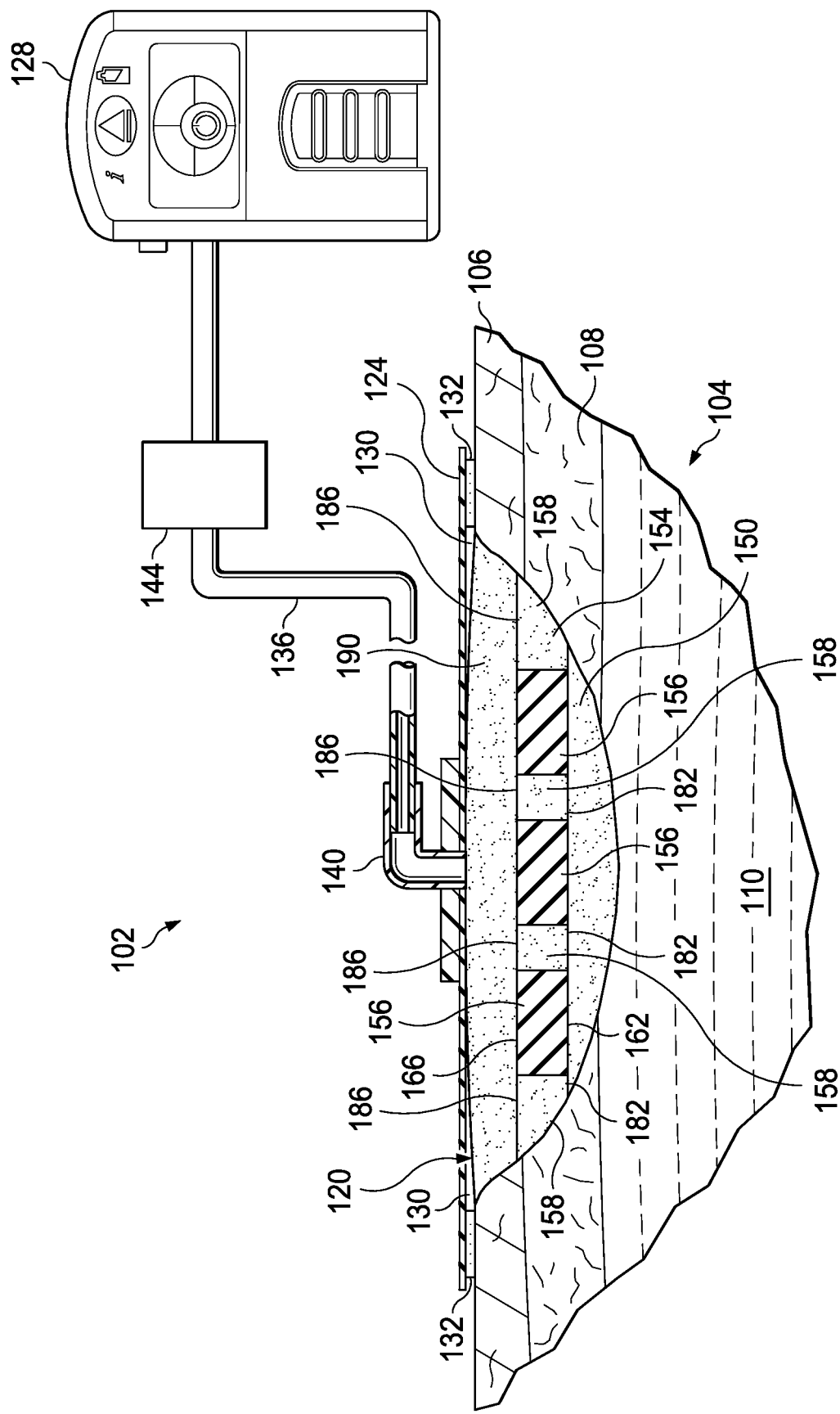
FIG. 1 is an illustrative embodiment of a treatment system for treating a sub-surface tissue site that depicts a cut-away view of an illustrative embodiment of a dressing according to this disclosure.
Figure 2:
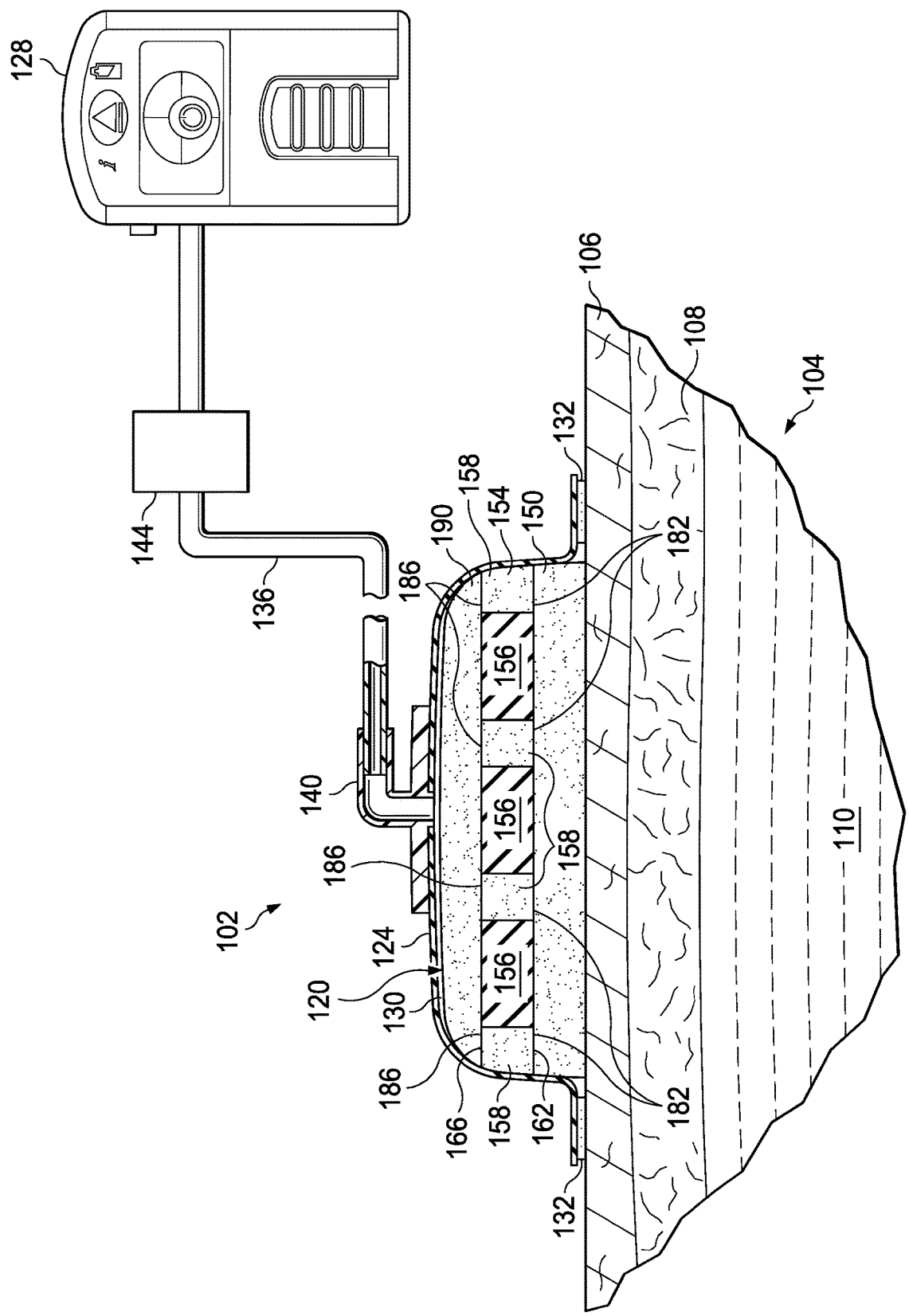
FIG. 2 depicts the treatment system and the dressing of FIG. 1 deployed on a surface tissue site.

Referring to the drawings, FIGS. 1 and 2 depict an illustrative embodiment of a treatment system 102 for treating a tissue site 104 of a patient. The tissue site 104 may extend through or otherwise involve an epidermis 106, a dermis 108, and a subcutaneous tissue 110. The tissue site 104 may be a sub-surface tissue site that extends below the surface of the epidermis 106, as depicted in FIG. 1. Further, the tissue site 104 may be a surface tissue site as depicted in FIG. 2 that predominantly resides on the surface of the epidermis 106. The treatment system 102 may provide therapy to, for example, the epidermis 106, dermis 108, and subcutaneous tissue 110, regardless of the positioning of the treatment system 102 or the type of tissue site. The treatment system 102 may also be utilized without limitation at other tissue sites.

The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 104 may include removal of fluids, e.g., exudate or ascites. As used herein, unless otherwise indicated, "or" does not require mutual exclusivity.

Continuing with FIGS. 1 and 2, the treatment system 102 may include a dressing 120, a sealing member 124, and a reduced-pressure source 128. The sealing member 124 may cover the dressing 120 at the tissue site 104 to provide a fluid seal and a sealed space 130 between the tissue site 104 and the sealing member 124. The sealing member 124 may cover the dressing 120 and a peripheral portion of the epidermis 106 surrounding the tissue site 104 to provide the fluid seal between the sealing member 124 and the tissue site 104. An adhesive 132 positioned, for example, about the tissue site 104 and between the sealing member 124 and the peripheral portion of the epidermis 106 may enhance the fluid seal between the sealing member 124 and the tissue site 104.

The sealing member 124 may be formed from any material that allows for a fluid seal. A fluid seal may be a seal adequate to maintain reduced pressure at a desired site given the particular reduced pressure source or system involved. The sealing member 124 may be sealed against the epidermis 106 or against a gasket or drape by a sealing apparatus, such as the adhesive 132. Further, the sealing apparatus may be an adhesive sealing tape, drape tape or strip, double-sided drape tape, pressure-sensitive adhesive, paste, hydrocolloid, or hydrogel, etc. If a tape is utilized, the tape may be formed of the same material as the sealing member 124 with a pre-applied, pressure-sensitive adhesive. The pressure-sensitive adhesive may be applied on a side of the sealing member 124 that faces the tissue site 104, or portion thereof.

The sealing member 124 may comprise, for example, one or more of the following materials: hydrophilic polyurethane; cellulosics; hydrophilic polyamides; an INSPIRE 2301 material from Expopack Advanced Coatings of Wrexham, United Kingdom; a thin, uncoated polymer drape; natural rubbers; polyisoprene; styrene butadiene rubber, chloroprene rubber, polybutadiene; nitrile rubber; butyl rubber; ethylene propylene rubber, ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material. The sealing member 124 may be a hybrid drape formed of a combination of the previously described materials and may have a lower silicone layer having perforated regions of exposed acrylic adhesive for securing the sealing member 124 about the tissue site 104 as previously described.

A conduit 136 may couple the reduced-pressure source 128 in fluid communication with the dressing 120. A conduit interface 140 may be coupled in fluid communication with the dressing 120, and may be adapted to connect the conduit 136 and the dressing 120 for providing fluid communication with the reduced-pressure source 128. The conduit interface 140 may be fluidly coupled to the conduit 136 in any suitable manner. The conduit interface 140 may be coupled to the sealing member 124 by an adhesive, for example. An aperture (not shown) in the sealing member 124 may provide fluid communication between the dressing 120 and the conduit interface 140. In other embodiments, the conduit 136 may be simply inserted into the dressing 120 through an aperture (not shown) in the sealing member 124 to provide fluid communication with the reduced-pressure source 128. The reduced-pressure source 128 may also be directly coupled in fluid communication with the dressing 120 and/or the sealing member 124.

The conduit interface 140 may be formed from a medical-grade, soft polymer or other pliable material. As non-limiting examples, the conduit interface 140 may be formed from polyurethane, polyethylene, polyvinyl chloride (PVC), fluorosilicone, ethylene-propylene, etc. In one illustrative, non-limiting embodiment, conduit interface 140 may be molded from DEHP-free PVC. The conduit interface 140 may be formed in any suitable manner such as by molding, casting, machining, or extruding. Further, the conduit interface 140 may be formed as an integral unit or as individual components.

A fluid canister 144 may be coupled in fluid communication between the reduced-pressure source 128 and the dressing 120. For example, the fluid canister 144 may be coupled in fluid communication with the conduit 136 between the reduced-pressure source 128 and the dressing 120. Positioning of the fluid canister 144 in this manner may permit the fluid canister 144 to retain fluid extracted from the tissue site 104. The fluid canister 144 may be any suitable container for retaining fluids from the tissue site 104.

As part of the treatment system 102, the reduced-pressure source 128 may provide reduced pressure to the dressing 120 and the sealed space 130. The reduced-pressure source 128 may be any suitable device for providing reduced pressure as described herein, such as, for example, a vacuum pump, wall suction, or other source.

As used herein, "reduced pressure" may refer to a pressure less than the ambient pressure at a tissue site being subjected to treatment. The reduced pressure may be less than the atmospheric pressure. The reduced pressure may also be less than a hydrostatic pressure at a tissue site. Unless otherwise indicated, values of pressure stated herein are gauge pressures. While the amount and nature of reduced pressure applied to a tissue site may vary according to the application, the reduced pressure may be between about −5 mm Hg to about −500 mm Hg. In some embodiments, the reduced pressure may be between about −100 mm Hg to about −200 mm Hg.

The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure may refer to a relative reduction in absolute pressure. An increase in reduced pressure may correspond to a reduction in pressure (more negative relative to ambient pressure), and a decrease in reduced pressure may correspond to an increase in pressure (less negative relative to ambient pressure).

Continuing with FIGS. 1 and 2, the dressing 120 may be adapted to distribute reduced pressure from the reduced-pressure source 128 to the tissue site 104. The dressing 120 may include a manifold layer 150, a storage layer 154, and a plurality of retainers 158. The manifold layer 150 may be adapted to be positioned proximate the tissue site 104, such as, for example, by cutting or otherwise shaping the manifold layer 150 in any suitable manner to fit the tissue site 104. As described below, the manifold layer 150 may be adapted to be positioned in fluid communication with the tissue site 104 to distribute reduced pressure to the tissue site 104. In some embodiments, the manifold layer 150 may be positioned in contact with the tissue site 104.

The manifold layer 150 may be formed from any manifold material or flexible bolster material that provides a vacuum space, or treatment space, such as, for example, a porous and permeable foam or foam-like material, a member formed with pathways, a graft, or a gauze. In some embodiments, the manifold layer 150 may be a reticulated, open-cell polyurethane or polyether foam that allows good permeability of fluids while under a reduced pressure. One such foam material is the VAC® GranuFoam® material available from Kinetic Concepts, Inc. (KCI) of San Antonio, Tex. The term "manifold" as used herein may refer to a substance or structure capable of applying reduced pressure to, delivering fluids to, or removing fluids from a tissue site. A manifold may include a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

A material with a higher or lower density than the GranuFoam® material may be desirable for the manifold layer 150 depending on the application. Among the many possible materials, the following may be used: GranuFoam® material, Foamex® technical foam (www.foamex.com), a molded bed of nails structure, a patterned grid material such as those manufactured by Sercol Industrial Fabrics, 3D textiles such as those manufactured by Baltex of Derby, U.K., a gauze, a flexible channel-containing member, or a graft. In some instances, ionic silver may be desirable to add to the foam by, for example, a micro bonding process. Other substances, such as antimicrobial agents, may be added to the foam as well.

In some embodiments, the manifold layer 150 may comprise a porous, hydrophobic material. Use of a hydrophobic material for the manifold layer 150 may prevent the manifold layer 150 from directly absorbing fluid, such as exudate, from the tissue site 104 while allowing the fluid to pass through.

The storage layer 154 may be positioned proximate the manifold layer 150. As described below, the storage layer 154 may be adapted to absorb fluid communicated from the tissue site 104 through the manifold layer 150. In some embodiments, at least a portion of the storage layer 154 may comprise an absorbent 156, such as, for example, a hydrophilic material capable of absorbing fluid and having an absorbent capacity suitable for a particular tissue site. The storage layer 154 may have a first surface 162 and an opposing second surface 166. The first surface 162 may be positioned proximate the manifold layer 150. In some embodiments, the first surface 162 of the storage layer 154 may be positioned in contact with the manifold layer 150.

The absorbent 156 may have a porous structure capable of providing fluid communication between the first surface 162 and the opposing second surface 166 of the storage layer 154. Materials that may be suitable for the absorbent 156 may include Luquafleece® material, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates.

Figure 3:
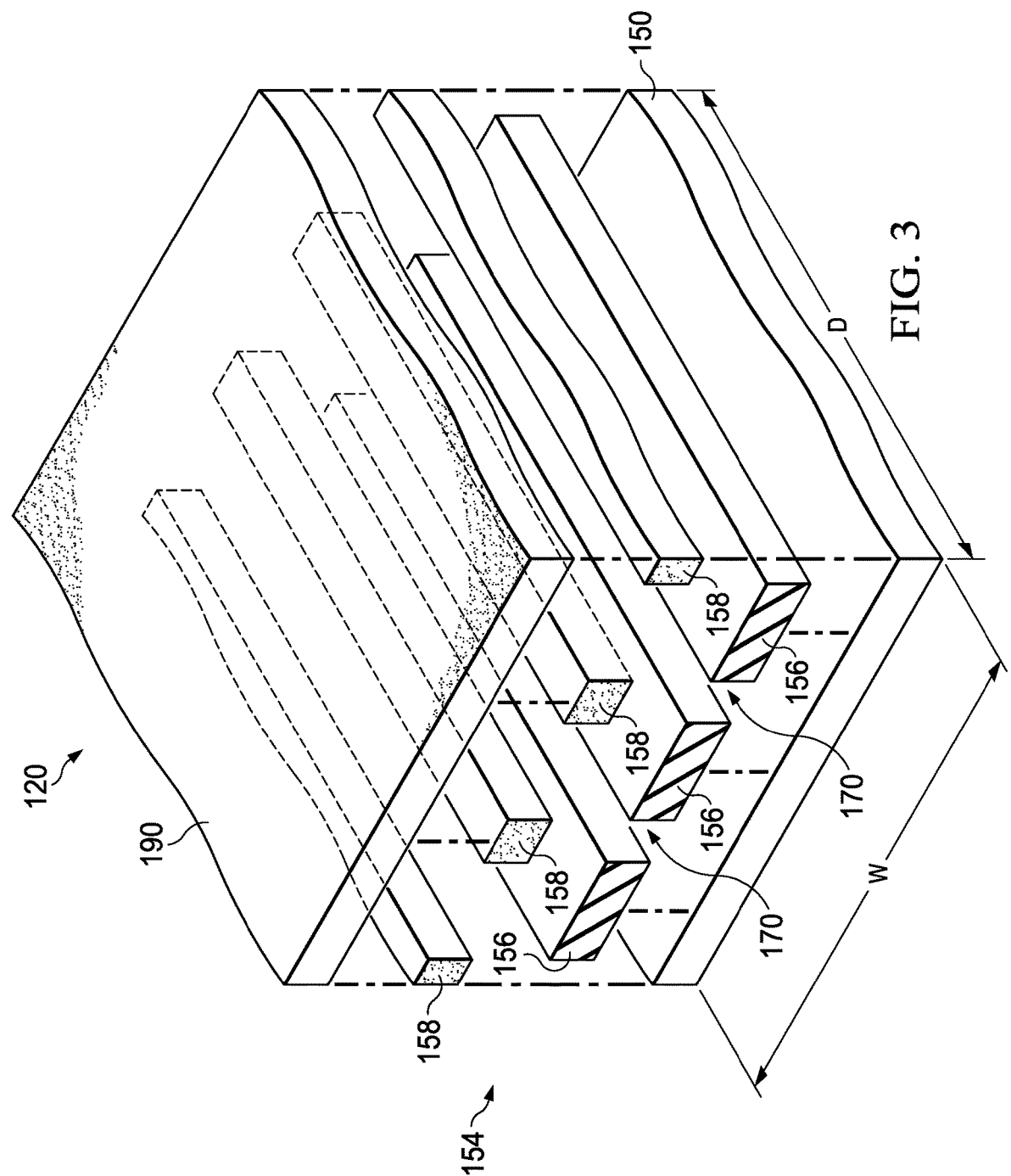
FIG. 3 is an exploded, perspective view of an illustrative embodiment of a dressing suitable for use as the dressing of FIG. 1.

As shown in FIG. 3, the absorbents 156 may be separated to provide one or more fluid communication channels 170 through the storage layer 154. A retainer 158 may be disposed in each of the fluid communication channels 170. The fluid communication channels 170 may be separate and distinguishable from any channels, pores, or passageways through the storage layer 154 that may be formed as a part of the material comprising the storage layer 154. In some embodiments, the fluid communication channels 170 may be defined by the retainers 158. As described herein, the retainers 158 may substantially preclude deformation of the storage layer 154 into the fluid communication channels 170, thereby substantially precluding blockage of the fluid communication channels 170 as the storage layer 154 absorbs fluid. In this manner, the retainers 158 may enhance fluid communication between the first surface 162 and the second surface 166 of the storage layer 154 independent of the amount of fluid being stored, retained, or otherwise absorbed by the storage layer 154.

In some embodiments, each of the fluid communication channels 170 may be in fluid communication with the manifold layer 150, and in fluid communication between the first and the second surfaces 162, 166 of the storage layer 154. For example, opposing ends of the fluid communication channels 170 may be substantially flush with the first surface 162 and the second surface 166 of the storage layer 154, respectively, such that one end of each of the fluid communication channels is proximate to the manifold layer 150.

In some embodiments, each of the retainers 158 may also extend between the first and the second surfaces 162, 166 of the storage layer 154. For example, a first end 182 of each of the retainers 158 may be positioned proximate to or in contact with the manifold layer 150. Further, a second end 186 of each of the retainers 158 may be substantially aligned with the opposing second surface 166 of the storage layer 154. The storage layer 154 may have a thickness defined between the first and the second surfaces 162, 166 of the storage layer 154. Each of the retainers 158 and the fluid communication channels 170 may extend through the thickness of the storage layer 154.

Although the drawings generally depict each of the retainers 158 as extending fully between the first and the second surfaces 162, 166 of the storage layer 154, other embodiments are possible. For example, the retainers 158 may be a helical wire having a spring-like shape inserted through the storage layer 154 and defining the fluid communication channels 170. Other embodiments for the retainers 158 may include a tubular structure disposed through the storage layer 154 for defining the fluid communication channels 170. Accordingly, the retainers 158 may extend fully between the first and the second surfaces 162, 166 of the storage layer 154, or merely through a sufficient portion of the storage layer 154 to provide the fluid communication channels 170. The type of the retainer 158 suitable for use may depend on the properties of the material chosen for the storage layer 154 and the ability of the retainer 158 to substantially preclude blockage of the fluid communication channels 170 as described herein.

Each of the retainers 158 may comprise a porous, hydrophobic material exhibiting similar properties as, for example, any of the hydrophobic materials described above in connection with the manifold layer 150. The retainers 158 may be comprised of the same or a different hydrophobic material than the manifold layer 150. In other embodiments, the retainers 158 may be, for example, a helical wire or tubular structure having an internal lumen as described above that is capable of substantially retaining or otherwise precluding the storage layer 154 from deforming into the fluid communication channels 170.

Referring to the illustrative embodiments of FIGS. 1-6B, the manifold layer 150 may be a first manifold layer 150 and the dressing 120 may additionally include a second manifold layer 190. The second manifold layer 190 may be positioned in fluid communication between the storage layer 154 and the sealing member 124.

Figure 4:
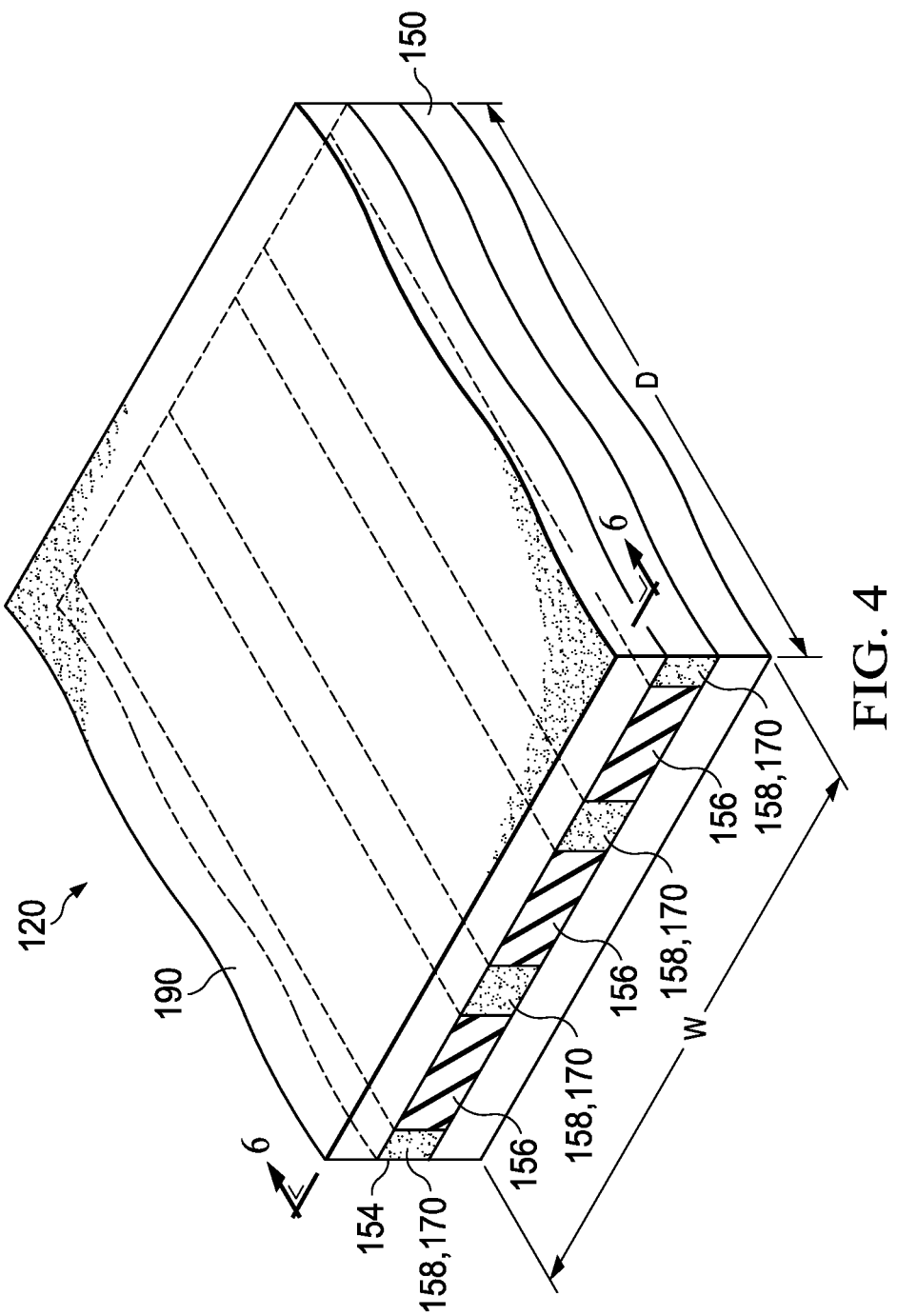
FIG. 4 is a perspective view of the dressing of FIG. 3.
Figure 5:
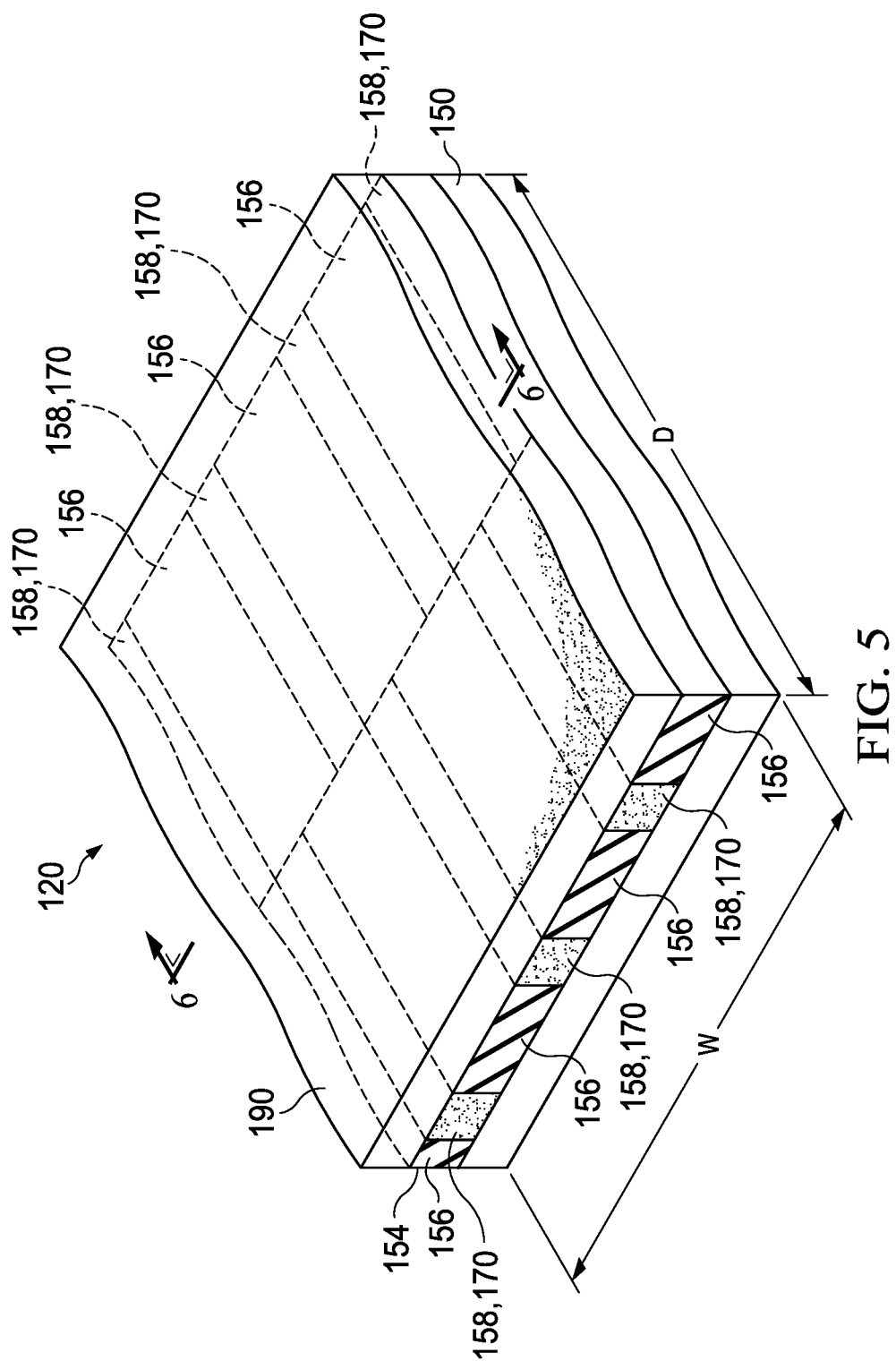
FIG. 5 is a perspective view of another illustrative embodiment of a dressing suitable for use as the dressing of FIG. 1.

Referring to FIGS. 4 and 5, FIGS. 4 and 5 depict illustrative embodiments of the dressing 120 in a substantially rectangular shape having a depth D and a width W positioned at substantially a right angle, or 90 degrees, relative to one another. However, the dressing 120 may have any shape suitable for a particular tissue site. Thus, in an embodiment of the dressing 120 having a circular or irregular shape, for example, the depth D and the width W may represent directions through a cross-section of the dressing 120, wherein the depth D is positioned at substantially a right angle, or 90 degrees, relative to the width W. Referring to FIG. 4, the storage layer 154 of the dressing 120 may have each of the retainers 158 positioned between two adjoining portions of the absorbent 156 along the width W of the storage layer 154. Continuing with FIG. 4, along the depth D, each of the retainers 158 and each of the portions of the absorbent 156 may extend substantially across the entire depth D. Referring now to FIG. 5, similar to FIG. 4, the storage layer 154 of the dressing 120 may have each of the retainers 158 positioned between two adjoining portions of the absorbent 156 along the width W of the storage layer 154. However, as depicted in FIG. 5, the retainers 158 may abut a portion of the absorbent 156 across the depth D. Similarly, the portions of the absorbent 156 may abut the retainers 158 across the depth D. Thus, as depicted in FIG.

5, the storage layer 154 of the dressing 120 may include the retainers 158 and the absorbent 156 positioned without limitation in any orientation across the depth D of the dressing 120. In either configuration along the depth D for the dressing 120 depicted in FIG. 4 or 5, at least a portion of the dressing 120 exhibits a cross-section and the elements depicted in FIGS. 1-2 and 6A-6B, as described above.

In operation, as the dressing 120 comes into contact with fluid from the tissue site 104, the storage layer 154 may wick the fluid through the manifold layer 150 and away from the tissue site 104. As described above, the manifold layer 150 may be adapted to communicate fluid from the tissue site 104 rather than store the fluid. Thus, relative to the manifold layer 150, the absorbent 156 in the storage layer 154 may exhibit absorbent properties that are more absorbent than any absorbent properties that may be exhibited by the manifold layer 150. The absorbent 156 being more absorbent than the manifold layer 150 may provide an absorbent gradient through the dressing 120 that may increase in absorbent capacity with increasing distance from the tissue site 104. Thus, the storage layer 154 may be adapted to wick, pull, draw, or otherwise attract fluid from the tissue site 104 through the manifold layer 150.

Figure 6A:
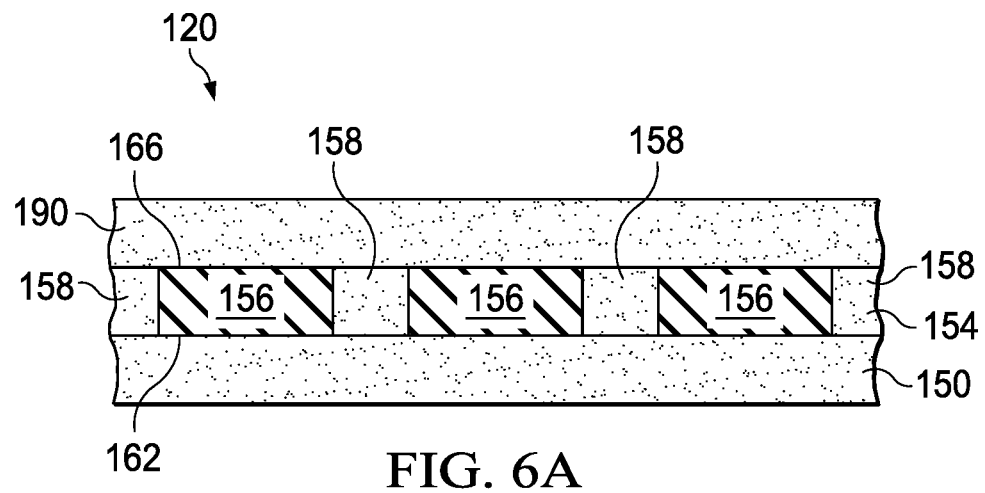
FIG. 6A is a cross-section view taken at line 6-6 in FIGS. 4 and 5, depicting the dressing of FIGS. 4 and 5 substantially free of fluid.
Figure 6B:
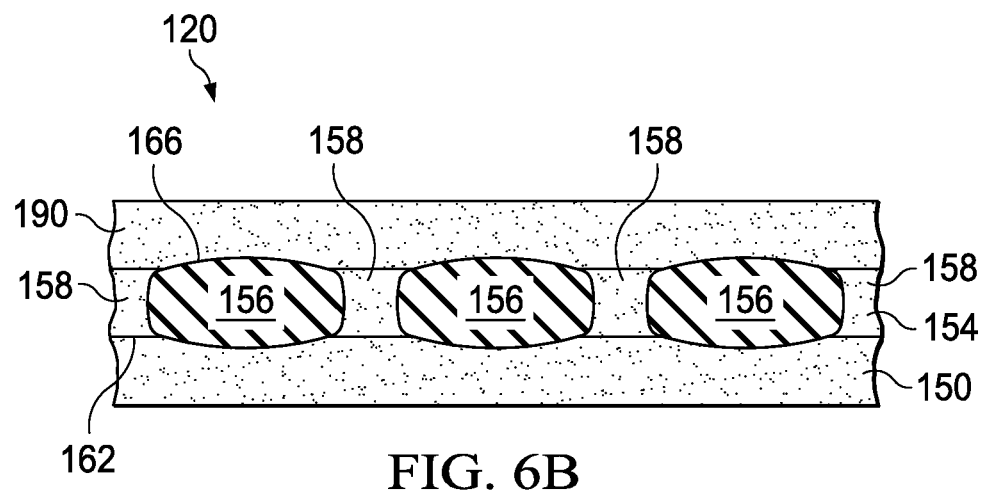
FIG. 6B is a cross-section view taken at line 6-6 in FIGS. 4 and 5, depicting the dressing of FIGS. 4 and 5 substantially saturated with fluid.

The dressing 120 may be deployed on the tissue site 104 initially as shown in FIG. 6A in a substantially unsaturated state. As the storage layer 154 in the dressing 120 wicks fluid from the tissue site 104 into the storage layer 154 for storage, the absorbent 156 in the storage layer 154 may swell as the fluid enters the storage layer 154 as depicted in FIG. 6B. Fluid saturation and swelling of the absorbent 156 in the storage layer 154 may reduce or substantially preclude the dressing 120 from maintaining fluid communication with the tissue site 104, causing a blockage. Thus, as shown in FIG. 6B, as the storage layer 154 in the dressing 120 becomes substantially saturated with fluid, the retainers 158 may substantially preclude the absorbent 156 from swelling or otherwise deforming into the fluid communication channels 170. In this manner, the retainers 158 may be adapted to maintain fluid communication between the first and the second surface 162, 166 of the storage layer 154 through the fluid communication channels 170. After the dressing 120 has reached a maximum fluid capacity or a substantially fluid saturated state, the retainers 158 and the fluid communication channels 170 may permit reduced pressure to reach the tissue site 104 to maintain reduced pressure therapy. Further, the retainers 158 may permit excess fluid to be drawn out of the dressing 120 through the fluid communication channels 170 to the fluid canister 144, thereby increasing the useable life of the dressing 120.

Figure 7:
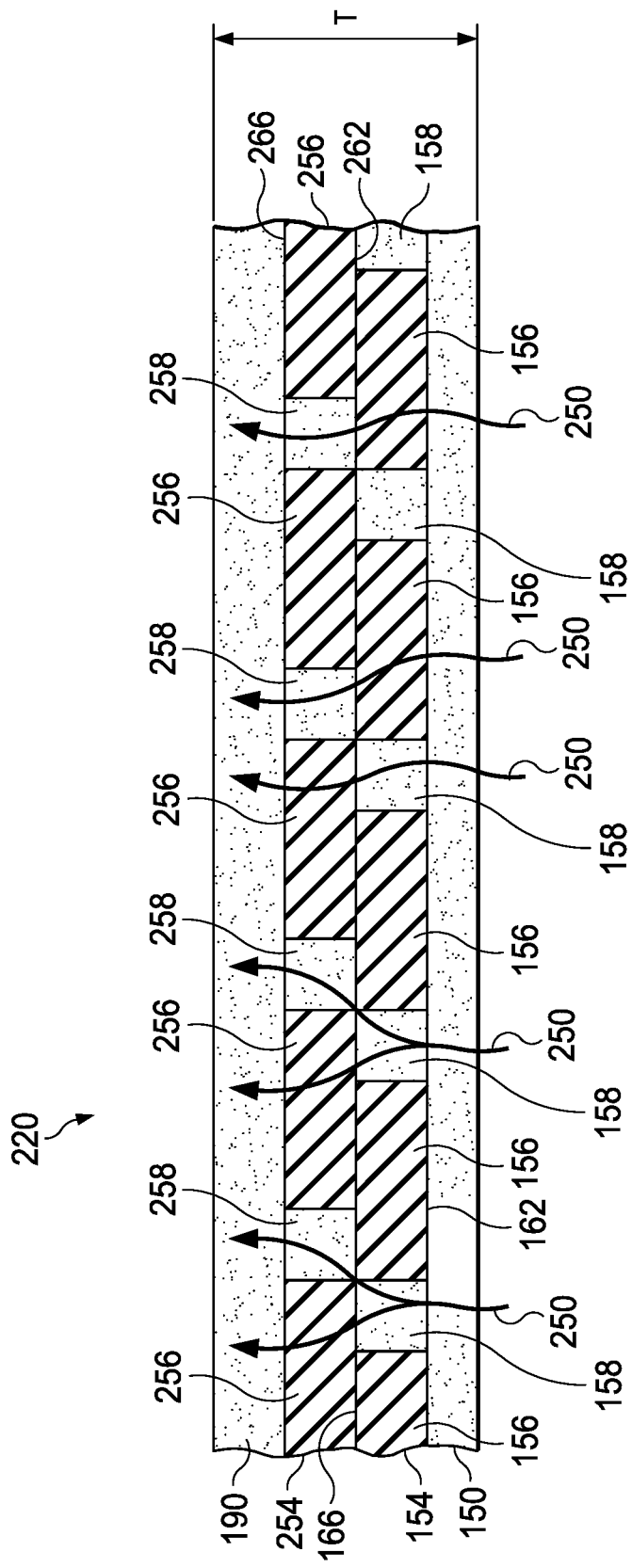
FIG. 7 is a cut-away view of another illustrative embodiment of a dressing suitable for use in the treatment system of FIG. 1.

Referring now to FIG. 7, FIG. 7 depicts an illustrative embodiment of a dressing 220 suitable for use in the treatment system 102 as previously described. The dressing 220 may include the first manifold layer 150, the second manifold layer 190, and the storage layer 154 having the absorbent 156. The retainers 158 may also be disposed in fluid communication channels through the storage layer 154 in this illustrative embodiment. However, the dressing 220 may additionally include a second storage layer 254 and a plurality of second retainers 258 disposed in the second storage layer 254 in substantially the same manner as described above in connection with the storage layer 154. The second retainers 258 may be disposed in second fluid communication channels in the second storage layer 254 in substantially the same manner as described above for the retainers 158. Similar to the retainers 158, the second retainers 258 may be adapted to substantially preclude deformation of an absorbent 256 into the second fluid communication channels. Further, the second storage layer 254 may be positioned in fluid communication with the storage layer 154 such that the second retainers 158 and the second fluid communication channels may be laterally offset from the first retainers 158 and the fluid communication channels in the first storage layer 154. For example, the retainers 158 may be laterally offset from the second retainers 258 by shifting the storage layer 154 and the second storage layer 254 relative to one another in a direction normal to a thickness T of the dressing 220. In some embodiments, the first manifold layer 150 may be adapted to be positioned in contact with the tissue site 104 such that the storage layer 154 may be disposed between the manifold layer 150 and the second storage layer 254.

Similar to the storage layer 154, at least a portion of the second storage layer 254 may comprise a hydrophilic material and may be adapted to absorb fluid communicated from the tissue site 104. Like the retainers 158, the second retainers 258 may comprise a porous, hydrophobic material as described above. Further, the second storage layer 254 may have a first surface 262 and an opposing second surface 266. The second fluid communication channels may be in fluid communication with the storage layer 154 and between the first surface 262 and the opposing second surface 266 of the second storage layer 254. In some embodiments, the second manifold layer 190 may be positioned proximate the second storage layer 254 and between the second storage layer 254 and the sealing member 124.

In operation, the dressing 220 may perform as described above in connection with the dressing 120. However, the second storage layer 254 in combination with the storage layer 154 may enhance the efficiency of the dressing 220 in distributing and communicating fluids in a substantially uniform manner. For example, the fluid communication channels in the storage layer 154 being laterally offset from the second fluid communication channels in the second storage layer 254 may encourage fluid to flow along multi-directional paths 250, as illustrated in FIG. 7. The multi-directional paths 250 may have a directional component that may be normal relative to the thickness T of the dressing 220, encouraging the fluid to move laterally within the storage layer 154 and the second storage layer 254 to contact the absorbents 156, 256. As deployed on the tissue site 104, the thickness T of the dressing 220 may be normal relative to the tissue site 104 such that a directional component of the multi-directional paths 250 may be along a surface of the tissue site 104. Similarly, lateral movement of the fluid in the multi-directional paths 250 may be along the first and the opposing second surface 162, 166 of the storage layer 154 and along the first and the opposing second surface 262, 266 of the second storage layer 254.

Figure 8:
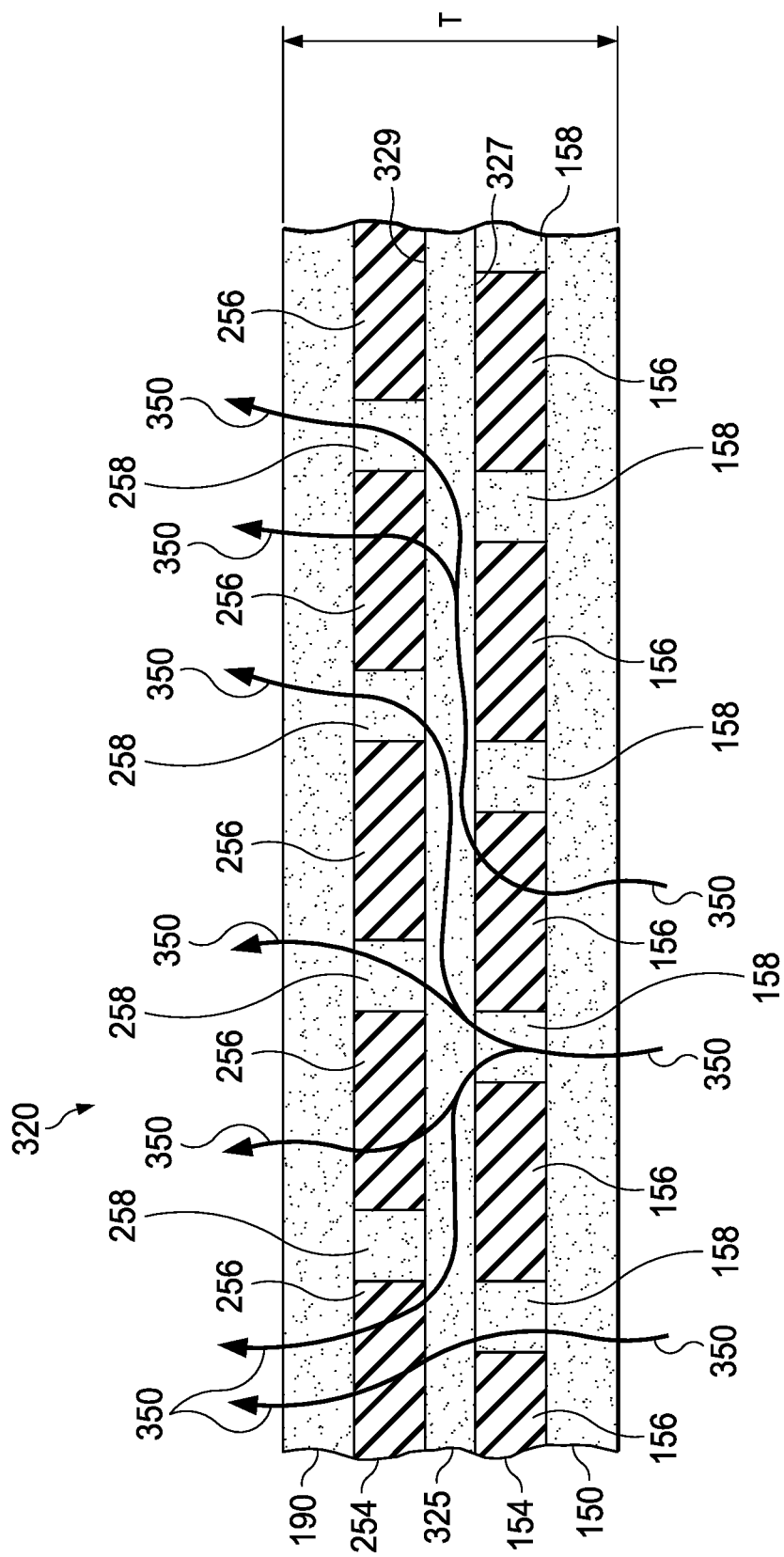
FIG. 8 is a cut-away view of yet another illustrative embodiment of a dressing suitable for use in the treatment system of FIG. 1.

Referring now to FIG. 8, FIG. 8 depicts an illustrative embodiment of a dressing 320 suitable for use in the treatment system 102 as previously described. The dressing 320 may include the first manifold layer 150, the second manifold layer 190, and the storage layer 154 having the retainers 158 disposed in fluid communication channels through the absorbent 156 as previously described. Further, the dressing 320 may include the second storage layer 254 having the second retainers 258 and the absorbent 256 as previously described. The second retainers 258 may be laterally offset from the retainers 158. The dressing 320 may additionally include an intermediate manifold layer 325 that may be positioned in fluid communication between the storage layer 154 and the second storage layer 254. As shown in FIG. 8, the retainers 158 may be positioned proximate a first surface 327 of the intermediate manifold layer 325 and the second retainers 258 may be positioned proximate an opposing second surface 329 of the intermediate manifold layer 325. The intermediate manifold layer 325 may comprise a porous, hydrophobic material similar to the porous, hydrophobic materials described above for the manifold layer 150 and the second manifold layer 190.

In operation, the dressing 320 can perform similar to the dressings 120 and 220 as described above. However, the intermediate manifold layer 325 may further enhance the efficiency of the dressing 320 in distributing and communicating fluids. For example, the intermediate manifold layer 325 may provide a lateral fluid communication passage between the storage layer 154 and the second storage layer 254. As described above, the fluid communication channels in the storage layer 154 may be laterally offset from the second fluid communication channels in the second storage layer 254. The fluid communication channels of the first storage layer 154 being laterally offset from the fluid communication channels of the second storage layer 154 may encourage fluid to flow along multi-directional paths 350, as shown in FIG. 8. The multi-directional paths 350 may have a directional component normal relative to a thickness T of the dressing 320, encouraging the fluid to move laterally within the storage layer 154 and the second storage layer 254 to contact the absorbents 156, 256. As deployed on the tissue site 104, the thickness T of the dressing 320 may be normal relative to the tissue site 104 such that a directional component of the multi-directional paths 350 may be along a surface of the tissue site 104. Similarly, lateral movement of the fluid in the multi-directional paths 350 may be along the first and the opposing second surface 162, 166 of the storage layer 154 and along the first and the opposing second surface 262, 266 of the second storage layer 254.

Figure 9:
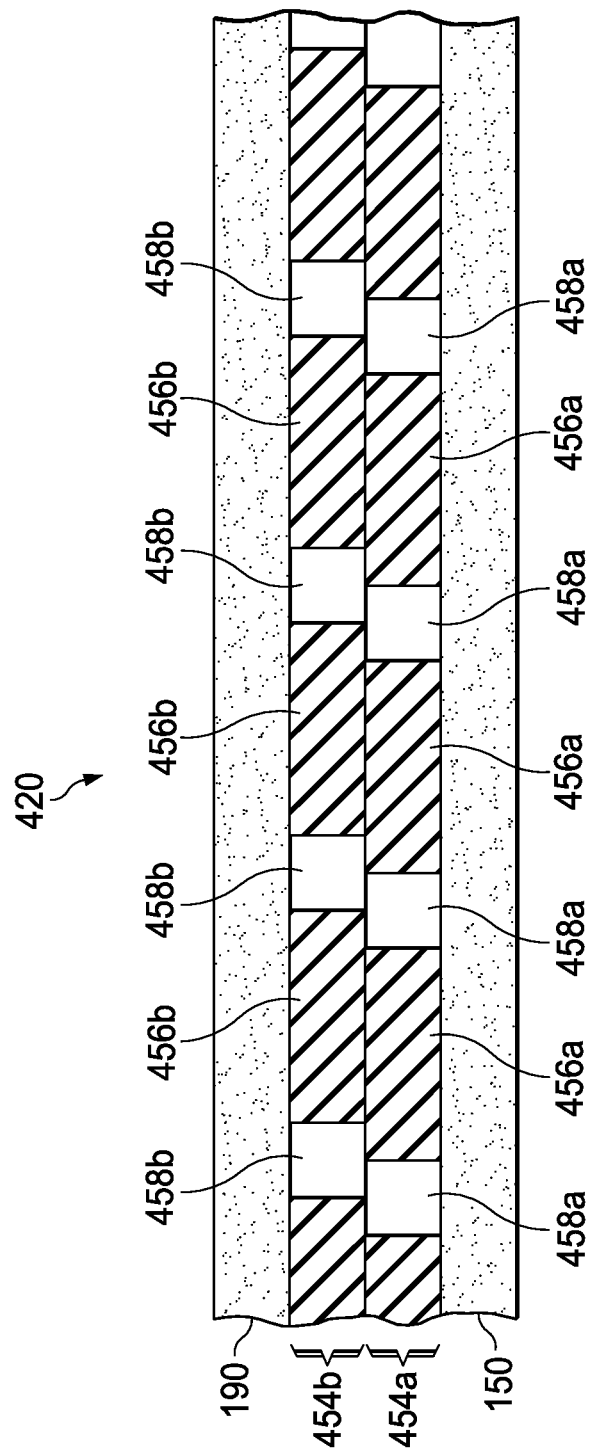
FIG. 9 is a cut-away view of yet another illustrative embodiment of a dressing suitable for use in the treatment system of FIG. 1.

Referring generally to FIG. 9, FIG. 9 depicts an illustrative embodiment of a dressing 420 suitable for use in the treatment system 102 as previously described. The dressing 420 provides an embodiment that may include a first storage layer 454a having a plurality of first apertures 458a and a second storage layer 454b having a plurality of second apertures 458b. As described further below, the first and the second storage layers 454a, 454b may be analogous to the storage layer 154 and the second storage layer 254, respectively. The dressing 420 may include other elements that may be analogous in positioning, characteristics, and operation as the previously described elements associated with the dressings 120, 220, and 320. For example, the dressing 420 may include the first manifold layer 150 and the second manifold layer 190 analogous to the dressings 120, 220, and 320. Although not shown in FIG. 9, the dressing 420 may also include the intermediate manifold layer 325 analogous to the dressing 320.

Referring to FIG. 9, the first storage layer 454a may be positioned proximate the first manifold layer 150 and may have the plurality of first apertures 458a disposed in the first storage layer 454a. Each of the first apertures 458a may provide fluid communication through the first storage layer 454a. The second storage layer 454b may be positioned in fluid communication with the first storage layer 454a and may have the plurality of second apertures 458b disposed in the second storage layer 454b. Each of the second apertures 458b may provide fluid communication through the second storage layer 454b. The first apertures 458a may be positioned in the dressing 420 laterally offset from the second apertures 458b. Thus, the first and the second apertures 458a, 458b may be analogous to the fluid communication channels 170 and the second fluid communication channels, respectively, described above.

In operation, the dressing 420 may perform similar to the dressings 120, 220, and 320 as described above, with the apertures 458a, 458b being of sufficient size to substantially preclude blockage of fluid communication through the first storage layer 454a and the second storage layer 454b. The required size of the apertures 458a, 458b may depend on the materials chosen for the first and the second storage layers 454a, 454b. The material for the first storage layer 454a may be an absorbent material 456a analogous to the materials previously described for the absorbent 156. The material for the second storage layer 454b may be an absorbent material 456b analogous to the materials previously described for the absorbent 256.

In other embodiments, the dressings 120, 220, 320, and 420 may include a collagen material (not shown). The collagen may, for example, be dispersed within a porous structure of the dressings 120, 220, 320, and 420 and be adapted to substantially preclude clogging of the porous structure. Further, the dressings 120, 220, 320, and 420 may include a composite ion-exchange resin (not shown) that may be adapted to react with sodium and chloride ions present in the dressings 120, 220, 320, and 420 to yield hydrogen and hydroxyl ions. The composite ion-exchange resin may be provided in the dressings 120, 220, 320, and 420 as a permeable membrane, or a as polymer coating on a woven or non-woven material.

This disclosure also provides a method for manufacturing a dressing, such as the dressings 120, 220, and 320. The method may include providing a manifold material, providing an absorbent material, and positioning the manifold material adjacent the absorbent material. Analogous to the manifolds 150 and 190, the manifold material may comprise the previously described hydrophobic materials. Analogous to the absorbents 156, 256, the absorbent material may comprise the previously described hydrophilic materials. Further, the method may include cutting across the manifold material and the absorbent material to form the first storage layer 154 and the second storage layer 254. The first and the second storage layer 154, 254 may each comprise at least portion of the manifold material and at least a portion of the absorbent material. Each portion of the manifold material in the storage layer 154 may provide the retainer 158 and each portion of the absorbent material in the storage layer 154 may provide the absorbent 156. Similarly, each portion of the manifold material in the storage layer 254 may provide the retainer 258 and each portion of the absorbent material in the storage layer 254 may provide the absorbent 256. Additionally, the method may provide for positioning the first storage layer 154 in fluid communication with the second storage layer 254 such that the portion of manifold material in the first storage layer 154 may be positioned laterally offset from the portion of manifold material in the second storage layer 254 as previously described.

Further, the method may include providing the manifold layer 150 that may be adapted to be positioned proximate the tissue site 104 and to distribute reduced pressure to the tissue site 104. The method may include positioning the manifold layer 150 proximate the first storage layer 154 such that the first storage layer 154 may be disposed in fluid communication between the manifold layer 150 and the second storage layer 254. The first and the second storage layers 154, 254 may be adapted to be in fluid communication with the tissue site 104 through the manifold layer 150.

Further, the method may include providing the second manifold layer 190 and positioning the second manifold layer 190 proximate the second storage layer 254. Even further, the method may include providing the intermediate manifold layer 325 and disposing the intermediate manifold layer 325 in fluid communication between the first and the second storage layers 154, 254.

Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

We claim:

1. A dressing adapted to distribute reduced pressure from a reduced-pressure source to a tissue site, comprising:
a storage layer adapted to absorb fluid communicated from the tissue site;
a fluid communication channel disposed through the storage layer; and
a retainer disposed in the fluid communication channel, wherein the retainer is adapted to substantially preclude deformation of the storage layer into the fluid communication channel, and wherein the retainer comprises a porous, hydrophobic material.

2. The dressing of claim 1, further comprising a manifold layer.

3. The dressing of claim 2, wherein the manifold layer is in fluid communication with the tissue site and adapted to distribute reduced pressure to the storage layer and the tissue site.

4. The dressing of claim 1, further comprising a sealing member and a manifold layer, wherein the sealing member is adapted to cover the dressing and to provide a fluid seal between the sealing member and the tissue site, and wherein the manifold layer is adapted to be positioned in fluid communication between the storage layer and the sealing member.

5. The dressing of claim 1, further comprising a conduit interface adapted to be coupled in fluid communication with the dressing and to provide fluid communication between the dressing and the reduced-pressure source.

6. The dressing of claim 1, further comprising a fluid canister in fluid communication between the reduced-pressure source and the dressing, the fluid canister adapted to retain fluid from the tissue site.

7. The dressing of claim 1, at least a portion of the storage layer comprising a hydrophilic material.

8. The dressing of claim 1, wherein the storage layer has a first surface and an opposing second surface, and wherein the fluid communication channel is in fluid communication between the first surface and the second surface of the storage layer.

9. The dressing of claim 1, wherein:
the storage layer is a first storage layer;
the retainer is a first retainer;
the fluid communication channel is a first fluid communication channel; and
the dressing further comprises a second storage layer, a second fluid communication channel disposed through the second storage layer, and a second retainer disposed in the second fluid communication channel, wherein the second retainer is adapted to substantially preclude deformation of the second storage layer into the second fluid communication channel, wherein the second storage layer is positioned in fluid communication with the first storage layer, and wherein the second fluid communication channel is laterally offset from the first fluid communication channel.

10. The dressing of claim 9, wherein at least a portion of the second storage layer comprises a hydrophilic material and is adapted to absorb fluid communicated from the tissue site, and wherein the second retainer comprises a porous, hydrophobic material.

11. The dressing of claim 9, wherein the second storage layer has a first surface and an opposing second surface, and wherein the second fluid communication channel is in fluid communication with the first storage layer and between the first surface and the second surface of the second storage layer.

12. The dressing of claim 9, wherein the dressing further comprises an intermediate manifold layer positioned in fluid communication between the first storage layer and the second storage layer, and wherein the first fluid communication channel is positioned proximate a first surface of the intermediate manifold layer and the second fluid communication channel is positioned proximate an opposing second surface of the intermediate manifold layer, the intermediate manifold layer comprising a porous, hydrophobic material.

13. The dressing of claim 1, the dressing further comprising collagen, wherein the dressing has a porous structure, and wherein the collagen is adapted to substantially preclude clogging of the porous structure.

* * * * *